(12) United States Patent
Lin et al.

(10) Patent No.: US 7,888,067 B2
(45) Date of Patent: Feb. 15, 2011

(54) RECOMBINANT HUMAN FACTOR IX AND USE THEREOF

(75) Inventors: Shu-Wha Lin, No. 1 Cheng-Te St., Taipei (TW) 100; Chia-Ni Lin, Taipei (TW); Hua-Lin Wu, Tainan (TW); Guey-Yueh Shi, Tainan (TW)

(73) Assignee: Shu-Wha Lin, Taipei (TW)

( * ) Notice: Subject to any disclaimer, the term of this patent is extended or adjusted under 35 U.S.C. 154(b) by 0 days.

(21) Appl. No.: 12/624,226

(22) Filed: Nov. 23, 2009

(65) Prior Publication Data

US 2010/0081712 A1 Apr. 1, 2010

Related U.S. Application Data

(63) Continuation of application No. 11/935,779, filed on Nov. 6, 2007, now Pat. No. 7,700,734.

(60) Provisional application No. 60/884,129, filed on Jan. 9, 2007.

(51) Int. Cl.
*C12P 21/06* (2006.01)
(52) U.S. Cl. .................. 435/69.1; 435/320.1; 435/6; 435/325; 530/350; 530/384
(58) Field of Classification Search .................. None
See application file for complete search history.

*Primary Examiner*—Hope A Robinson
(74) *Attorney, Agent, or Firm*—WPAT, P.C.; Anthony King

(57) ABSTRACT

The present invention aims at converting factor IX into a molecule with enhanced activity which provides an alternative for replacement therapy and gene therapy for hemophilia B. Using recombinant techniques, factor IX with replacement at positions 86, 277, and 338 exhibits better clotting activity than recombinant wild type factor IX.

6 Claims, 2 Drawing Sheets

SEQUENCE LISTING

```
<160> NUMBER OF SEQ ID NOS: 24

<210> SEQ ID NO 1
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-1

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60
```

-continued

```
Asp Ile Asn Ser Tyr Glu Cys Trp Cys Pro Phe Gly Phe Glu Gly Lys
 65                  70                  75                  80

Asn Cys Glu Leu Asp Ala Thr Cys Asn Ile Lys Asn Gly Arg Cys Glu
             85                  90                  95

Gln Phe Cys Lys Asn Ser Ala Asp Asn Lys Val Val Cys Ser Cys Thr
        100                 105                 110

Glu Gly Tyr Arg Leu Ala Glu Asn Gln Lys Ser Cys Glu Pro Ala Val
    115                 120                 125

Pro Phe Pro Cys Gly Arg Val Ser Val Ser Gln Thr Ser Lys Leu Thr
130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```

<210> SEQ ID NO 2
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-2

<400> SEQUENCE: 2

Tyr Asn Ser Gly Lys Leu Glu Glu Phe Val Gln Gly Asn Leu Glu Arg

```
1               5                   10                  15
Glu Cys Met Glu Glu Lys Cys Ser Phe Glu Glu Ala Arg Glu Val Phe
                20                  25                  30
Glu Asn Thr Glu Arg Thr Thr Glu Phe Trp Lys Gln Tyr Val Asp Gly
                35                  40                  45
Asp Gln Cys Glu Ser Asn Pro Cys Leu Asn Gly Gly Ser Cys Lys Asp
                50                  55                  60
Asp Ile Asn Ser Tyr Glu Cys Trp Cys Pro Phe Gly Phe Glu Gly Lys
65                      70                  75                  80
Asn Cys Glu Leu Asp Val Thr Cys Asn Ile Lys Asn Gly Arg Cys Glu
                    85                  90                  95
Gln Phe Cys Lys Asn Ser Ala Asp Asn Lys Val Val Cys Ser Cys Thr
                100                 105                 110
Glu Gly Tyr Arg Leu Ala Glu Asn Gln Lys Ser Cys Glu Pro Ala Val
                115                 120                 125
Pro Phe Pro Cys Gly Arg Val Ser Val Ser Gln Thr Ser Lys Leu Thr
                130                 135                 140
Arg Ala Glu Thr Val Phe Pro Asp Val Asp Tyr Val Asn Ser Thr Glu
145                 150                 155                 160
Ala Glu Thr Ile Leu Asp Asn Ile Thr Gln Ser Thr Gln Ser Phe Asn
                    165                 170                 175
Asp Phe Thr Arg Val Val Gly Gly Glu Asp Ala Lys Pro Gly Gln Phe
                180                 185                 190
Pro Trp Gln Val Val Leu Asn Gly Lys Val Asp Ala Phe Cys Gly Gly
                195                 200                 205
Ser Ile Val Asn Glu Lys Trp Ile Val Thr Ala Ala His Cys Val Glu
                210                 215                 220
Thr Gly Val Lys Ile Thr Val Val Ala Gly Glu His Asn Ile Glu Glu
225                 230                 235                 240
Thr Glu His Thr Glu Gln Lys Arg Asn Val Ile Arg Ile Ile Pro His
                    245                 250                 255
His Asn Tyr Asn Ala Ala Ile Asn Lys Tyr Asn His Asp Ile Ala Leu
                260                 265                 270
Leu Glu Leu Asp Ala Pro Leu Val Leu Asn Ser Tyr Val Thr Pro Ile
                275                 280                 285
Cys Ile Ala Asp Lys Glu Tyr Thr Asn Ile Phe Leu Lys Phe Gly Ser
                290                 295                 300
Gly Tyr Val Ser Gly Trp Gly Arg Val Phe His Lys Gly Arg Ser Ala
305                 310                 315                 320
Leu Val Leu Gln Tyr Leu Arg Val Pro Leu Val Asp Arg Ala Thr Cys
                    325                 330                 335
Leu Arg Ser Thr Lys Phe Thr Ile Tyr Asn Asn Met Phe Cys Ala Gly
                    340                 345                 350
Phe His Glu Gly Gly Arg Asp Ser Cys Gln Gly Asp Ser Gly Gly Pro
                355                 360                 365
His Val Thr Glu Val Glu Gly Thr Ser Phe Leu Thr Gly Ile Ile Ser
                370                 375                 380
Trp Gly Glu Glu Cys Ala Met Lys Gly Lys Tyr Gly Ile Tyr Thr Lys
385                 390                 395                 400
Val Ser Arg Tyr Val Asn Trp Ile Lys Glu Lys Thr Lys Leu Thr
                    405                 410                 415

<210> SEQ ID NO 3
```

-continued

```
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-3

<400> SEQUENCE: 3
```

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Ala Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Ala Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

```
His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 4
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-4

<400> SEQUENCE: 4

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Ala Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
```

```
                305                 310                 315                 320
Leu Val Leu Gln Tyr Leu Arg Val Pro Leu Val Asp Arg Ala Thr Cys
                325                 330                 335

Leu Ala Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
                370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 5
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-5

<400> SEQUENCE: 5

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
                35                  40                  45

Asp Gln Cys Glu Ser Asn Pro Cys Leu Asn Gly Gly Ser Cys Lys Asp
                50                  55                  60

Asp Ile Asn Ser Tyr Glu Cys Trp Cys Pro Phe Gly Phe Glu Gly Lys
65              70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
                100                 105                 110

Glu Gly Tyr Arg Leu Ala Glu Asn Gln Lys Ser Cys Glu Pro Ala Val
                115                 120                 125

Pro Phe Pro Cys Gly Arg Val Ser Val Ser Gln Thr Ser Lys Leu Thr
                130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
                180                 185                 190

Pro Trp Gln Val Val Leu Asn Gly Lys Val Asp Ala Phe Cys Gly Gly
                195                 200                 205

Ser Ile Val Asn Glu Lys Trp Ile Val Thr Ala Ala His Cys Val Glu
                210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255
```

-continued

His Asn Tyr Asn Ala Ala Ile Asn Lys Tyr Asn His Asp Ile Ala Leu
            260                 265                 270

Leu Glu Leu Asp Ala Pro Leu Val Leu Asn Ser Tyr Val Thr Pro Ile
275                 280                 285

Cys Ile Ala Asp Lys Glu Tyr Thr Asn Ile Phe Leu Lys Phe Gly Ser
            290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Ala Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
            370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 6
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-6

<400> SEQUENCE: 6

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
50                  55                  60

Asp Ile Asn Ser Tyr Glu Cys Trp Cys Pro Phe Gly Phe Glu Gly Lys
65                  70                  75                  80

Asn Cys Glu Leu Asp Ala Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

```
Pro Trp Gln Val Val Leu Asn Gly Lys Val Asp Ala Phe Cys Gly Gly
            195                 200                 205

Ser Ile Val Asn Glu Lys Trp Ile Val Thr Ala Ala His Cys Val Glu
210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Ala Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Ala Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 7
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-7

<400> SEQUENCE: 7

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
```

-continued

```
                  130                 135                 140
Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```

<210> SEQ ID NO 8
<211> LENGTH: 415
<212> TYPE: PRT
<213> ORGANISM: Homo sapiens
<220> FEATURE:
<221> NAME/KEY: Protein
<222> LOCATION: (1)..(415)
<223> OTHER INFORMATION: IX-8

<400> SEQUENCE: 8

```
Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80
```

```
Asn Cys Glu Leu Asp Val Thr Cys Asn Ile Lys Asn Gly Arg Cys Glu
                 85                  90                  95
Gln Phe Cys Lys Asn Ser Ala Asp Asn Lys Val Val Cys Ser Cys Thr
            100                 105                 110
Glu Gly Tyr Arg Leu Ala Glu Asn Gln Lys Ser Cys Glu Pro Ala Val
        115                 120                 125
Pro Phe Pro Cys Gly Arg Val Ser Val Ser Gln Thr Ser Lys Leu Thr
    130                 135                 140
Arg Ala Glu Thr Val Phe Pro Asp Val Asp Tyr Val Asn Ser Thr Glu
145                 150                 155                 160
Ala Glu Thr Ile Leu Asp Asn Ile Thr Gln Ser Thr Gln Ser Phe Asn
                165                 170                 175
Asp Phe Thr Arg Val Val Gly Gly Glu Asp Ala Lys Pro Gly Gln Phe
            180                 185                 190
Pro Trp Gln Val Val Leu Asn Gly Lys Val Asp Ala Phe Cys Gly Gly
        195                 200                 205
Ser Ile Val Asn Glu Lys Trp Ile Val Thr Ala Ala His Cys Val Glu
    210                 215                 220
Thr Gly Val Lys Ile Thr Val Val Ala Gly Glu His Asn Ile Glu Glu
225                 230                 235                 240
Thr Glu His Thr Glu Gln Lys Arg Asn Val Ile Arg Ile Ile Pro His
                245                 250                 255
His Asn Tyr Asn Ala Ala Ile Asn Lys Tyr Asn His Asp Ile Ala Leu
            260                 265                 270
Leu Glu Leu Asp Glu Pro Leu Val Leu Asn Ser Tyr Val Thr Pro Ile
        275                 280                 285
Cys Ile Ala Asp Lys Glu Tyr Thr Asn Ile Phe Leu Lys Phe Gly Ser
    290                 295                 300
Gly Tyr Val Ser Gly Trp Gly Arg Val Phe His Lys Gly Arg Ser Ala
305                 310                 315                 320
Leu Val Leu Gln Tyr Leu Arg Val Pro Leu Val Asp Arg Ala Thr Cys
                325                 330                 335
Leu Ala Ser Thr Lys Phe Thr Ile Tyr Asn Asn Met Phe Cys Ala Gly
            340                 345                 350
Phe His Glu Gly Gly Arg Asp Ser Cys Gln Gly Asp Ser Gly Gly Pro
        355                 360                 365
His Val Thr Glu Val Glu Gly Thr Ser Phe Leu Thr Gly Ile Ile Ser
    370                 375                 380
Trp Gly Glu Glu Cys Ala Met Lys Gly Lys Tyr Gly Ile Tyr Thr Lys
385                 390                 395                 400
Val Ser Arg Tyr Val Asn Trp Ile Lys Glu Lys Thr Lys Leu Thr
                405                 410                 415

<210> SEQ ID NO 9
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-1

<400> SEQUENCE: 9
atgcagcgcg tgaacatgat catggcagaa tcaccaggcc tcatcaccat ctgccttta      60 ggatatctac tcagtgctga atgtacagtt tttcttgatc atgaaaacgc caacaaaatt     120
```

-continued

| | |
|---|---|
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgcaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttcc tgatgtggac | 600 |
| tatgtaaatt ctactgaagc tgaaaccatt ttggataaca tcactcaaag cacccaatca | 660 |
| tttaatgact tcactcgggt tgttggtgga aagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |
| ctggacgaac ccttagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga gatcagcttt agttcttcag taccttagag ttccacttgt tgaccgagcc | 1140 |
| acatgtcttc gatctacaaa gttcaccatc tataacaaca tgttctgtgc tggcttccat | 1200 |
| gaaggaggta gagattcatg tcaaggagat agtggggac cccatgttac tgaagtggaa | 1260 |
| gggaccagtt tcttaactgg aattattagc tggggtgaag agtgtgcaat gaaaggcaaa | 1320 |
| tatggaatat ataccaaggt atcccggtat gtcaactgga ttaaggaaaa aacaaagctc | 1380 |
| acttaatgaa agatggattt ccaaggttaa ttcattggaa ttgaaaatta acagggcctc | 1440 |
| tcactaacta atcactttcc catctttgt tagatttgaa tatatacatt ctatgatcat | 1500 |
| tgcttttct ctttacaggg gagaatttca tattttacct gagcaaattg attagaaaat | 1560 |
| ggaaccacta gaggaatata atgtgttagg aaattacagt catttctaag ggcccagccc | 1620 |
| ttgacaaaat tgtgaagtta aattctccac tctgtccatc agatactatg gttctccact | 1680 |
| atggcaacta actcactcaa ttttccctcc ttagcagcat tccatcttcc cgatcttctt | 1740 |
| tgcttctcca accaaaacat caatgtttat tagttctgta tacagtacag gatctttggt | 1800 |
| ctactctatc acaaggccag taccacactc atgaagaaag aacacaggag tagctgagag | 1860 |
| gctaaaactc atcaaaaaca ctactccttt tcctctaccc tattcctcaa tcttttacct | 1920 |
| tttccaaatc ccaatcccca aatcagtttt tctctttctt actccctctc tccctttttac | 1980 |
| cctccatggt cgttaaagga gagatgggga gcatcattct gttatacttc tgtacacagt | 2040 |
| tatacatgtc tatcaaaccc agacttgctt ccatagtgga gacttgcttt tcagaacata | 2100 |
| gggatgaagt aaggtgcctg aaaagtttgg gggaaaagtt tctttcagag agttaagtta | 2160 |
| ttttatatat ataatatata tataaaatat ataatataca atataaatat atagtgtgtg | 2220 |
| tgtgtatgcg tgtgtgtaga cacacacgca tacacacata taatgaaagc aataagccat | 2280 |
| tctaagagct tgtatggtta tggaggtctg actaggcatg atttcacgaa ggcaagattg | 2340 |
| gcatatcatt gtaactaaaa aagctgcat tgacccagac atattgtact ctttctaaaa | 2400 |
| ataataataa taatgctaac agaaagaaga gaaccgttcg tttgcaatct acagctagta | 2460 |

-continued

| gagactttga ggaagaattc aacagtgtgt cttcagcagt gttcagagcc aagcaagaag | 2520 |
| ttgaagttgc ctagaccaga ggacataagt atcatgtctc ctttaactag catacccga | 2580 |
| agtggagaag ggtgcagcag gctcaaaggc ataagtcatt ccaatcagcc aactaagttg | 2640 |
| tccttttctg gtttcgtgtt caccatggaa cattttgatt atagttaatc cttctatctt | 2700 |
| gaatcttcta gagagttgct gaccaactga cgtatgtttc cctttgtgaa ttaataaact | 2760 |
| ggtgttctgg ttcat | 2775 |

<210> SEQ ID NO 10
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-2

<400> SEQUENCE: 10

| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt tggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactagggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |
| ctggacgcac ccttagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga atcagcttt agttcttcag taccttagag ttccacttgt tgaccgagcc | 1140 |
| acatgtcttc gatctacaaa gttcaccatc tataacaaca tgttctgtgc tggcttccat | 1200 |
| gaaggaggta gagattcatg tcaaggagat agtgggggac ccatgttac tgaagtggaa | 1260 |
| gggaccagtt tcttaactgg aattattagc tggggtgaag agtgtgcaat gaaaggcaaa | 1320 |
| tatggaatat ataccaaggt atcccggtat gtcaactgga ttaaggaaaa aacaaagctc | 1380 |
| acttaatgaa agatggattt ccaaggttaa ttcattggaa ttgaaaatta cagggcctc | 1440 |
| tcactaacta atcactttcc catctttgt tagatttgaa tatatacatt ctatgatcat | 1500 |
| tgcttttct ctttacaggg gagaatttca tatttttacct gagcaaattg attagaaaat | 1560 |
| ggaaccacta gaggaatata atgtgttagg aaattacagt catttctaag ggcccagccc | 1620 |
| ttgacaaaat tgtgaagtta aattctccac tctgtccatc agatactatg gttctccact | 1680 |

-continued

| | |
|---|---|
| atggcaacta actcactcaa ttttccctcc ttagcagcat ccatcttcc cgatcttctt | 1740 |
| tgcttctcca accaaaacat caatgtttat tagttctgta tacagtacag gatctttggt | 1800 |
| ctactctatc acaaggccag taccacactc atgaagaaag aacacaggag tagctgagag | 1860 |
| gctaaaactc atcaaaaaca ctactccttt tcctctaccc tattcctcaa tcttttacct | 1920 |
| tttccaaatc ccaatcccca aatcagtttt tctctttctt actccctctc tcccttttac | 1980 |
| cctccatggt cgttaaagga gagatgggga gcatcattct gttatacttc tgtacacagt | 2040 |
| tatacatgtc tatcaaaccc agacttgctt ccatagtgga gacttgcttt tcagaacata | 2100 |
| gggatgaagt aaggtgcctg aaaagtttgg gggaaaagtt tctttcagag agttaagtta | 2160 |
| ttttatatat ataatatata tataaaatat ataatataca atataaatat atagtgtgtg | 2220 |
| tgtgtatgcg tgtgtgtaga cacacacgca tacacacata taatggaagc aataagccat | 2280 |
| tctaagagct tgtatggtta tggaggtctg actaggcatg atttcacgaa ggcaagattg | 2340 |
| gcatatcatt gtaactaaaa aagctgacat tgacccagac atattgtact ctttctaaaa | 2400 |
| ataataataa taatgctaac agaaagaaga gaaccgttcg tttgcaatct acagctagta | 2460 |
| gagactttga ggaagaattc aacagtgtgt cttcagcagt gttcagagcc aagcaagaag | 2520 |
| ttgaagttgc ctagaccaga ggacataagt atcatgtctc ctttaactag catacccga | 2580 |
| agtggagaag ggtgcagcag gctcaaaggc ataagtcatt ccaatcagcc aactaagttg | 2640 |
| tcctttctg gtttcgtgtt caccatggaa catttgatt atagttaatc cttctatctt | 2700 |
| gaatcttcta gagagttgct gaccaactga cgtatgtttc cctttgtgaa ttaataaact | 2760 |
| ggtgttctgg ttcat | 2775 |

<210> SEQ ID NO 11
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-3

<400> SEQUENCE: 11

| | |
|---|---|
| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgcaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |

-continued

```
gaacataata ttgaggagac agaacataca gagcaaaagc gaaatgtgat tcgaattatt      900
cctcaccaca actacaatgc agctattaat aagtacaacc atgacattgc ccttctggaa      960
ctggacgcac ccttagtgct aaacagctac gttacaccta tttgcattgc tgacaaggaa     1020
tacacgaaca tcttcctcaa atttggatct ggctatgtaa gtggctgggg aagagtcttc     1080
cacaaaggga gatcagcttt agttcttcag taccttagag ttccacttgt tgaccgagcc     1140
acatgtcttc gatctacaaa gttcaccatc tataacaaca tgttctgtgc tggcttccat     1200
gaaggaggta gagattcatg tcaaggagat agtgggggac cccatgttac tgaagtggaa     1260
gggaccagtt tcttaactgg aattattagc tggggtgaag agtgtgcaat gaaaggcaaa     1320
tatggaatat ataccaaggt atcccggtat gtcaactgga ttaaggaaaa aacaaagctc     1380
acttaatgaa agatggattt ccaaggttaa ttcattggaa ttgaaaatta cagggcctc      1440 tcactaacta atcactttcc catcttttgt tagatttgaa tatatacatt ctatgatcat     1500 tgcttttttct ctttacaggg gagaatttca tattttacct gagcaaattg attagaaaat    1560
ggaaccacta gaggaatata atgtgttagg aaattacagt catttctaag ggcccagccc     1620
ttgacaaaat tgtgaagtta aattctccac tctgtccatc agatactatg gttctccact     1680
atggcaacta actcactcaa ttttccctcc ttagcagcat tccatcttcc cgatcttctt     1740
tgcttctcca accaaaacat caatgttat tagttctgta tacagtacag gatctttggt      1800
ctactctatc acaaggccag taccacactc atgaagaaag aacacaggag tagctgagag     1860
gctaaaactc atcaaaaaca ctactccttt tcctctaccc tattcctcaa tcttttacct     1920
tttccaaatc ccaatcccca atcagttttt tctctttctt actccctctc tcccttttac    1980
cctccatggt cgttaaagga gagatgggga gcatcattct gttatacttc tgtacacagt     2040
tatacatgtc tatcaaaccc agacttgctt ccatagtgga gacttgcttt tcagaacata     2100
gggatgaagt aaggtgcctg aaaagtttgg gggaaaagtt tctttcagag agttaagtta     2160
ttttatatat ataatatata tataaaatat ataatataca atataaatat atagtgtgtg     2220
tgtgtatgcg tgtgtgtaga cacacacgca tacacacata taatgaaagc aataagccat     2280
tctaagagct tgtatggtta tggaggtctg actaggcatg atttcacgaa ggcaagattg     2340
gcatatcatt gtaactaaaa aagctgacat tgacccagac atattgtact ctttctaaaa     2400
ataataataa taatgctaac agaaagaaga gaaccgttcg tttgcaatct acagctagta     2460
gagactttga ggaagaattc aacagtgtgt cttcagcagt gttcagagcc aagcaagaag     2520
ttgaagttgc ctagaccaga ggacataagt atcatgtctc ctttaactag catacccga      2580 agtggagaag ggtgcagcag gctcaaaggc ataagtcatt ccaatcagcc aactaagttg     2640
tccttttctg gtttcgtgtt caccatgaa catttttgatt atagttaatc cttctatctt    2700
gaatcttcta gagagttgct gaccaactga cgtatgtttc cctttgtgaa ttaataaact     2760
ggtgttctgg ttcat                                                    2775
```

<210> SEQ ID NO 12
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-4

<400> SEQUENCE: 12

```
atgcagcgcg tgaacatgat catggcagaa tcaccaggcc tcatcaccat ctgccttta        60
```

-continued

```
ggatatctac tcagtgctga atgtacagtt tttcttgatc atgaaaacgc caacaaaatt      120
ctgaatcggc caaagaggta taattcaggt aaattggaag agtttgttca agggaacctt      180
gagagagaat gtatggaaga aaagtgtagt tttgaagaag cacgagaagt ttttgaaaac      240
actgaaagaa caactgaatt ttggaagcag tatgttgatg gagatcagtg tgagtccaat      300
ccatgtttaa atggcggcag ttgcaaggat gacattaatt cctatgaatg ttggtgtccc      360
tttggatttg aaggaaagaa ctgtgaatta gatgcaacat gtaacattaa aatggcaga     420 tgcgagcagt tttgtaaaaa tagtgctgat aacaaggtgg tttgctcctg tactgaggga      480
tatcgacttg cagaaaacca gaagtcctgt gaaccagcag tgccatttcc atgtggaaga      540
gtttctgttt cacaaacttc taagctcacc cgtgctgaga ctgttttttcc tgatgtggac      600 tatgtaaatt ctactgaagc tgaaaccatt ttggataaca tcactcaaag cacccaatca      660
tttaatgact tcactcgggt tgttggtgga aagatgccaa accaggtcaa attcccttgg      720
caggttgttt tgaatggtaa agttgatgca ttctgtggag gctctatcgt taatgaaaaa      780
tggattgtaa ctgctgccca ctgtgttgaa actggtgtta aaattacagt tgtcgcaggt      840
gaacataata ttgaggagac agaacataca gagcaaaagc gaaatgtgat tcgaattatt      900
cctcaccaca actacaatgc agctattaat aagtacaacc atgacattgc ccttctggaa      960
ctggacgaac ccttagtgct aaacagctac gttacaccta tttgcattgc tgacaaggaa     1020
tacacgaaca tcttcctcaa atttggatct ggctatgtaa gtggctgggg aagagtcttc     1080
cacaaaggga atcagctttt agttcttcag taccttagag ttccacttgt tgaccgagcc     1140
acatgtcttg catctacaaa gttcaccatc tataacaaca tgttctgtgc tggcttccat     1200
gaaggaggta gagattcatg tcaaggagat agtgggggac cccatgttac tgaagtggaa     1260
gggaccagtt tcttaactgg aattattagc tggggtgaag agtgtgcaat gaaaggcaaa     1320
tatggaatat ataccaaggt atcccggtat gtcaactgga ttaaggaaaa aacaaagctc     1380
acttaatgaa agatggattt ccaaggttaa ttcattggaa ttgaaaatta cagggcctc     1440 tcactaacta atcactttcc catcttttgt tagatttgaa tatatacatt ctatgatcat     1500
tgctttttct ctttacaggg gagaatttca tatttacct gagcaaattg attagaaaat     1560
ggaaccacta gaggaatata atgtgttagg aaattacagt catttctaag ggccccagccc     1620 ttgacaaaat tgtgaagtta aattctccac tctgtccatc agatactatg gttctccact     1680
atggcaacta actcactcaa ttttccctcc ttagcagcat tccatcttcc cgatcttctt     1740
tgcttctcca accaaaacat caatgtttat tagttctgta tacagtacag gatctttggt     1800
ctactctatc acaaggccag taccacactc atgaagaaag aacacaggag tagctgagag     1860
gctaaaactc atcaaaaaca ctactccttt tcctctaccc tattcctcaa tcttttacct     1920
tttccaaatc ccaatcccca aatcagtttt tctctttctt actccctctc tccctttac      1980 cctccatggt cgttaaagga gagatgggga gcatcattct gttatacttc tgtacacagt     2040
tatacatgtc tatcaaaccc agacttgctt ccatagtgga gacttgcttt tcagaacata     2100
gggatgaagt aaggtgcctg aaaagtttgg gggaaaagtt tctttcagag agttaagtta     2160
ttttatatat ataatatata tataaaatat ataatataca atataaatat atagtgtgtg     2220
tgtgtatgcg tgtgtgtaga cacacacgca tacacacata taatggaagc aataagccat     2280
tctaagagct tgtatggtta tggaggtctg actaggcatg atttcacgaa ggcaagattg     2340
gcatatcatt gtaactaaaa aagctgacat tgacccagac atattgtact ctttctaaaa     2400
```

-continued

| | |
|---|---|
| ataataataa taatgctaac agaaagaaga gaaccgttcg tttgcaatct acagctagta | 2460 |
| gagactttga ggaagaattc aacagtgtgt cttcagcagt gttcagagcc aagcaagaag | 2520 |
| ttgaagttgc ctagaccaga ggacataagt atcatgtctc ctttaactag catacccega | 2580 |
| agtggagaag ggtgcagcag gctcaaaggc ataagtcatt ccaatcagcc aactaagttg | 2640 |
| tccttttctg gtttcgtgtt caccatggaa catttttgatt atagttaatc cttctatctt | 2700 |
| gaatcttcta gagagttgct gaccaactga cgtatgtttc cctttgtgaa ttaataaact | 2760 |
| ggtgttctgg ttcat | 2775 |

<210> SEQ ID NO 13
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-5

<400> SEQUENCE: 13

| | |
|---|---|
| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |
| ctggacgcac ccttagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga tcagctttag ttcttcag taccttagag ttccacttgt tgaccgagcc | 1140 |
| acatgtcttg catctacaaa gttcaccatc tataacaaca tgttctgtgc tggcttccat | 1200 |
| gaaggaggta gagattcatg tcaaggagat agtggggac cccatgttac tgaagtggaa | 1260 |
| gggaccagtt tcttaactgg aattattagc tggggtgaag agtgtgcaat gaaaggcaaa | 1320 |
| tatggaatat ataccaaggt atcccggtat gtcaactgga ttaaggaaaa aacaaagctc | 1380 |
| acttaatgaa agatggattt ccaaggttaa ttcattggaa ttgaaaatta cagggcctc | 1440 |
| tcactaacta atcactttcc catctttgt tagatttgaa tatatacatt ctatgatcat | 1500 |
| tgctttttct ctttacaggg gagaatttca tattttacct gagcaaattg attagaaaat | 1560 |
| ggaaccacta gaggaatata atgtgttagg aaattacagt catttctaag ggcccagccc | 1620 |

```
ttgacaaaat tgtgaagtta aattctccac tctgtccatc agatactatg gttctccact    1680
atggcaacta actcactcaa ttttccctcc ttagcagcat tccatcttcc cgatcttctt    1740
tgcttctcca accaaaacat caatgtttat tagttctgta tacagtacag gatctttggt    1800
ctactctatc acaaggccag taccacactc atgaagaaag aacacaggag tagctgagag    1860
gctaaaactc atcaaaaaca ctactccttt tcctctaccc tattcctcaa tcttttacct    1920
tttccaaatc ccaatcccca atcagttttt tctctttctt actccctctc tccttttac    1980 cctccatggt cgttaaagga gagatgggga gcatcattct gttatacttc tgtacacagt    2040
tatacatgtc tatcaaaccc agacttgctt ccatagtgga gacttgcttt tcagaacata    2100
gggatgaagt aaggtgcctg aaaagtttgg gggaaaagtt tctttcagag agttaagtta    2160
ttttatatat ataatatata tataaaatat ataatataca atataaatat atagtgtgtg    2220
tgtgtatgcg tgtgtgtaga cacacacgca tacacacata taatgaaagc aataagccat    2280
tctaagagct tgtatggtta tggaggtctg actaggcatg atttcacgaa ggcaagattg    2340
gcatatcatt gtaactaaaa aagctgacat tgacccagac atattgtact ctttctaaaa    2400
ataataataa taatgctaac agaaagaaga gaaccgttcg tttgcaatct acagctagta    2460
gagactttga ggaagaattc aacagtgtgt cttcagcagt gttcagagcc aagcaagaag    2520
ttgaagttgc ctagaccaga ggacataagt atcatgtctc ctttaactag catacccga    2580 agtggagaag ggtgcagcag gctcaaaggc ataagtcatt ccaatcagcc aactaagttg    2640
tccttttctg gtttcgtgtt caccatgaaa cattttgatt atagttaatc cttctatctt    2700
gaatcttcta gagagttgct gaccaactga cgtatgtttc cctttgtgaa ttaataaact    2760
ggtgttctgg ttcat                                                    2775

<210> SEQ ID NO 14
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-6

<400> SEQUENCE: 14
atgcagcgcg tgaacatgat catggcagaa tcaccaggcc tcatcaccat ctgccttta     60 ggatatctac tcagtgctga atgtacagtt tttcttgatc atgaaaacgc caacaaaatt    120
ctgaatcggc caaagaggta taattcaggt aaattggaag agtttgttca agggaacctt    180
gagagagaat gtatggaaga aaagtgtagt tttgaagaag cacgagaagt ttttgaaaac    240
actgaaagaa caactgaatt ttggaagcag tatgttgatg gagatcagtg tgagtccaat    300
ccatgtttaa atggcggcag ttgcaaggat gacattaatt cctatgaatg ttggtgtccc    360
tttggatttg aaggaagaa ctgtgaatta gatgcaacat gtaacattaa gaatggcaga    420
tgcgagcagt tttgtaaaaa tagtgctgat aacaaggtgg tttgctcctg tactgaggga    480
tatcgacttg cagaaaacca gaagtcctgt gaaccagcag tgccattcc atgtggaaga    540 gtttctgttt cacaaacttc taagctcacc cgtgctgaga ctgttttcc tgatgtggac    600 tatgtaaatt ctactgaagc tgaaaccatt ttggataaca tcactcaaag cacccaatca    660
tttaatgact tcactcgggt tgttggtgga agatgccca aaccaggtca attcccttgg    720
caggttgttt tgaatggtaa agttgatgca ttctgtggag gctctatcgt taatgaaaaa    780
```

```
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgcac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttg catctacaaa gttcaccatc tataacaaca tgttctgtgc tggcttccat   1200
gaaggaggta gagattcatg tcaaggagat agtgggggac cccatgttac tgaagtggaa   1260
gggaccagtt tcttaactgg aattattagc tggggtgaag agtgtgcaat gaaaggcaaa   1320 tatgaatat ataccaaggt atcccggtat gtcaactgga ttaaggaaaa aacaaagctc   1380
acttaatgaa agatggattt ccaaggttaa ttcattggaa ttgaaaatta cagggcctc   1440 tcactaacta atcactttcc catcttttgt tagatttgaa tatatacatt ctatgatcat   1500
tgctttttct ctttacaggg gagaatttca tattttacct gagcaaattg attagaaaat   1560
ggaaccacta gaggaatata atgtgttagg aaattacagt catttctaag ggcccagccc   1620
ttgacaaaat tgtgaagtta aattctccac tctgtccatc agatactatg gttctccact   1680
atggcaacta actcactcaa ttttccctcc ttagcagcat tccatcttcc cgatcttctt   1740
tgcttctcca accaaaacat caatgtttat tagttctgta tacagtacag gatctttggt   1800
ctactctatc acaaggccag taccacactc atgaagaaag aacacaggag tagctgagag   1860
gctaaaactc atcaaaaaca ctactccttt tcctctaccc tattcctcaa tcttttacct   1920
tttccaaatc ccaatcccca aatcagtttt tctctttctt actccctctc tccctttac   1980 cctccatggt cgttaaagga gagatgggga gcatcattct gttatacttc tgtacacagt   2040
tatacatgtc tatcaaaccc agacttgctt ccatagtgga gacttgcttt tcagaacata   2100
gggatgaagt aaggtgcctg aaaagtttgg gggaaaagtt tctttcagag agttaagtta   2160
ttttatatat ataatatata tataaaaatat ataatataca atataaatat atagtgtgtg   2220
tgtgtatgcg tgtgtgtaga cacacacgca tacacacata taatggaagc aataagccat   2280
tctaagagct tgtatggtta tggaggtctg actaggcatg atttcacgaa ggcaagattg   2340
gcatatcatt gtaactaaaa aagctgacat tgacccagac atattgtact ctttctaaaa   2400
ataataataa taatgctaac agaaagaaga gaaccgttcg tttgcaatct acagctagta   2460
gagactttga ggaagaattc aacagtgtgt cttcagcagt gttcagagcc aagcaagaag   2520
ttgaagttgc ctagaccaga ggacataagt atcatgtctc ctttaactag catacccga   2580 agtggagaag ggtgcagcag gctcaaaggc ataagtcatt ccaatcagcc aactaagttg   2640
tccttttctg gtttcgtgtt caccatggaa catttgatt atagttaatc cttctatctt   2700
gaatcttcta gagagttgct gaccaactga cgtatgtttc cctttgtgaa ttaataaact   2760
ggtgttctgg ttcat                                                    2775
```

<210> SEQ ID NO 15
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-7

<400> SEQUENCE: 15

-continued

```
atgcagcgcg tgaacatgat catggcagaa tcaccaggcc tcatcaccat ctgcctttta    60
ggatatctac tcagtgctga atgtacagtt tttcttgatc atgaaaacgc caacaaaatt   120
ctgaatcggc caaagaggta taattcaggt aaattggaag agtttgttca agggaacctt   180
gagagagaat gtatggaaga aaagtgtagt tttgaagaag cacgagaagt tttgaaaaac   240
actgaaagaa caactgaatt ttggaagcag tatgttgatg gagatcagtg tgagtccaat   300
ccatgtttaa atggcggcag ttgcaaggat acattaatt cctatgaatg ttggtgtccc    360
tttggatttg aaggaaagaa ctgtgaatta gatgtaacat gtaacattaa gaatggcaga   420
tgcgagcagt tttgtaaaaa tagtgctgat aacaaggtgg tttgctcctg tactgaggga   480
tatcgacttg cagaaaacca gaagtcctgt gaaccagcag tgccatttcc atgtggaaga   540
gtttctgttt cacaaacttc taagctcacc cgtgctgaga ctgtttttcc tgatgtggac   600
tatgtaaatt ctactgaagc tgaaaccatt ttggataaca tcactcaaag cacccaatca   660
tttaatgact tcactcgggt tgttggtgga aagatgcca aaccaggtca attcccttgg    720
caggttgttt tgaatggtaa agttgatgca ttctgtggag ctctatcgt taatgaaaaa    780
tggattgtaa ctgctgccca ctgtgttgaa actggtgtta aaattacagt tgtcgcaggt   840
gaacataata ttgaggagac agaacataca gagcaaaagc gaaatgtgat tcgaattatt   900
cctcaccaca actacaatgc agctattaat aagtacaacc atgacattgc ccttctggaa   960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga atcagctttt agttcttcag taccttagag ttccacttgt tgaccgagcc  1140
acatgtcttc gatctacaaa gttcaccatc tataacaaca tgttctgtgc tggcttccat  1200
gaaggaggta gagattcatg tcaaggagat agtgggggac ccatgttac tgaagtggaa   1260
gggaccagtt tcttaactgg aattattagc tggggtgaag agtgtgcaat gaaaggcaaa  1320
tatggaatat ataccaaggt atcccggtat gtcaactgga ttaaggaaaa aacaaagctc  1380
acttaatgaa agatggattt ccaaggttaa ttcattggaa ttgaaaatta cagggcctc   1440
tcactaacta atcactttcc catcttttgt tagatttgaa tatatacatt ctatgatcat  1500
tgcttttct ctttacaggg gagaatttca tattttacct gagcaaattg attagaaaat   1560
ggaaccacta gaggaatata atgtgttagg aaattacagt catttctaag ggcccagccc  1620
ttgacaaaat tgtgaagtta aattctccac tctgtccatc agatactatg gttctccact  1680
atggcaacta actcactcaa ttttccctcc ttagcagcat tccatcttcc cgatcttctt  1740
tgcttctcca accaaaacat caatgtttat tagttctgta tacagtacag gatctttggt  1800
ctactctatc acaaggccag taccacactc atgaagaaag aacacaggag tagctgagag  1860
gctaaaactc atcaaaaaca ctactccttt tcctctaccc tattcctcaa tcttttacct  1920
tttccaaatc ccaatcccca aatcagtttt tctctttctt actccctctc tccctttac   1980
cctccatggt cgttaaagga gagatgggga gcatcattct gttatacttc tgtacacagt  2040
tatacatgtc tatcaaaccc agacttgctt ccatagtgga gacttgcttt tcagaacata  2100
gggatgaagt aaggtgcctg aaaagtttgg gggaaaagtt tctttcagag agttaagtta  2160
ttttatatat ataatatata tataaaatat ataaatataca atataaatat atagtgtgtg  2220
tgtgtatgcg tgtgtgtaga cacacacgca tacacacata taatgaaagc aataagccat  2280
tctaagagct tgtatggtta tggaggtctg actaggcatg atttcacgaa ggcaagattg  2340
```

```
gcatatcatt gtaactaaaa aagctgacat tgacccagac atattgtact ctttctaaaa   2400
ataataataa taatgctaac agaaagaaga gaaccgttcg tttgcaatct acagctagta   2460
gagactttga ggaagaattc aacagtgtgt cttcagcagt gttcagagcc aagcaagaag   2520
ttgaagttgc ctagaccaga ggacataagt atcatgtctc ctttaactag catacccga   2580 agtggagaag ggtgcagcag gctcaaaggc ataagtcatt ccaatcagcc aactaagttg   2640 tcctttctg gtttcgtgtt caccatggaa cattttgatt atagttaatc cttctatctt    2700
gaatcttcta gagagttgct gaccaactga cgtatgtttc cctttgtgaa ttaataaact   2760
ggtgttctgg ttcat                                                    2775
```

<210> SEQ ID NO 16
<211> LENGTH: 2775
<212> TYPE: DNA
<213> ORGANISM: Homo sapiens
<220> FEATURE:
<221> NAME/KEY: DNA
<222> LOCATION: (1)..(2775)
<223> OTHER INFORMATION: IX-8

<400> SEQUENCE: 16

```
atgcagcgcg tgaacatgat catggcagaa tcaccaggcc tcatcaccat ctgccttta     60 ggatatctac tcagtgctga atgtacagtt tttcttgatc atgaaaacgc caacaaaatt   120
ctgaatcggc caaagaggta taattcaggt aaattggaag agtttgttca agggaacctt   180
gagagagaat gtatggaaga aaagtgtagt tttgaagaag cacgagaagt ttttgaaaac   240
actgaaagaa caactgaatt ttggaagcag tatgttgatg gagatcagtg tgagtccaat   300
ccatgtttaa atggcggcag ttgcaaggat gacattaatt cctatgaatg ttggtgtccc   360
tttggatttg aaggaaagaa ctgtgaatta gatgtaacat gtaacattaa gaatggcaga   420
tgcgagcagt tttgtaaaaa tagtgctgat aacaaggtgg tttgctcctg tactgaggga   480
tatcgacttg cagaaaacca gaagtcctgt gaaccagcag tgccatttcc atgtggaaga   540
gtttctgttt cacaaacttc taagctcacc cgtgctgaga ctgttttcc tgatgtggac   600 tatgtaaatt ctactgaagc tgaaaccatt ttggataaca tcactcaaag cacccaatca   660
tttaatgact tcactcgggt tgttggtgga gaagatgcca aaccaggtca attcccttgg   720
caggttgttt tgaatggtaa agttgatgca ttctgtggag gctctatcgt taatgaaaaa   780
tggattgtaa ctgctgccca ctgtgttgaa actggtgtta aaattacagt tgtcgcaggt   840
gaacataata ttgaggagac agaacataca gagcaaaagc gaaatgtgat tcgaattatt   900
cctcaccaca actacaatgc agctattaat aagtacaacc atgacattgc ccttctggaa   960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga tcagctttt agttcttcag taccttagag ttccacttgt tgaccgagcc  1140
acatgtcttg catctacaaa gttcaccatc tataacaaca tgttctgtgc tggcttccat  1200
gaaggaggta gagattcatg tcaaggagat agtggggac cccatgttac tgaagtggaa  1260
gggaccagtt tcttaactgg aattattagc tggggtgaag agtgtgcaat gaaaggcaaa  1320
tatggaatat ataccaaggt atcccggtat gtcaactgga ttaaggaaaa acaaagctc   1380 acttaatgaa agatggattt ccaaggttaa tcattggaa ttgaaaatta cagggcctc    1440 tcactaacta atcactttcc catctttgt tagatttgaa tatatacatt ctatgatcat   1500 tgcttttct ctttacaggg gagaatttca tatttacct gagcaaattg attagaaaat    1560
```

-continued

```
ggaaccacta gaggaatata atgtgttagg aaattacagt catttctaag ggcccagccc   1620
ttgacaaaat tgtgaagtta aattctccac tctgtccatc agatactatg gttctccact   1680
atggcaacta actcactcaa ttttccctcc ttagcagcat tccatcttcc cgatcttctt   1740
tgcttctcca accaaaacat caatgtttat tagttctgta tacagtacag gatctttggt   1800
ctactctatc acaaggccag taccacactc atgaagaaag aacacaggag tagctgagag   1860
gctaaaactc atcaaaaaca ctactccttt tcctctaccc tattcctcaa tcttttacct   1920
tttccaaatc ccaatcccca aatcagtttt tctctttctt actccctctc tcccttttac   1980
cctccatggt cgttaaagga gagatgggga gcatcattct gttatacttc tgtacacagt   2040
tatacatgtc tatcaaaccc agacttgctt ccatagtgga gacttgcttt tcagaacata   2100
gggatgaagt aaggtgcctg aaaagtttgg gggaaaagtt tctttcagag agttaagtta   2160
ttttatatat ataatatata tataaaatat ataatataca atataaatat atagtgtgtg   2220
tgtgtatgcg tgtgtgtaga cacacacgca tacacacata taatggaagc aataagccat   2280
tctaagagct tgtatggtta tggaggtctg actaggcatg atttcacgaa ggcaagattg   2340
gcatatcatt gtaactaaaa aagctgacat tgacccagac atattgtact ctttctaaaa   2400
ataataataa taatgctaac agaaagaaga gaaccgttcg tttgcaatct acagctagta   2460
gagactttga ggaagaattc aacagtgtgt cttcagcagt gttcagagcc aagcaagaag   2520
ttgaagttgc ctagaccaga ggacataagt atcatgtctc ctttaactag catacccga   2580 agtggagaag ggtgcagcag gctcaaaggc ataagtcatt ccaatcagcc aactaagttg   2640
tccttttctg gtttcgtgtt caccatggaa catttttgatt atagttaatc cttctatctt   2700
gaatcttcta gagagttgct gaccaactga cgtatgtttc cctttgtgaa ttaataaact   2760
ggtgttctgg ttcat                                                   2775
```

```
<210> SEQ ID NO 17
<211> LENGTH: 21
<212> TYPE: DNA
<213> ORGANISM: Artificial
<220> FEATURE:
<223> OTHER INFORMATION: one of the primer pairs for replacing
      residue 86 on the human factor IX cDNA.
<220> FEATURE:
<221> NAME/KEY: misc_binding
<222> LOCATION: (1)..(21)

<400> SEQUENCE: 17
gtgaattaga tgcaacatgt a                                              21

<210> SEQ ID NO 18
<211> LENGTH: 24
<212> TYPE: DNA
<213> ORGANISM: Artificial
<220> FEATURE:
<223> OTHER INFORMATION: one of the primer pairs for replacing
      residue 86 on the human factor IX cDNA.
<220> FEATURE:
<221> NAME/KEY: misc_binding
<222> LOCATION: (1)..(24)

<400> SEQUENCE: 18
tgttacatgt tgcatctaat tcac                                           24

<210> SEQ ID NO 19
<211> LENGTH: 22
<212> TYPE: DNA
```

```
<213> ORGANISM: Artificial
<220> FEATURE:
<223> OTHER INFORMATION: one of the primer pairs for replacing
      residue 277 on the human factor IX cDNA.
<220> FEATURE:
<221> NAME/KEY: misc_binding
<222> LOCATION: (1)..(22)

<400> SEQUENCE: 19
gaactggacg caccctttagt gc                                              22

<210> SEQ ID NO 20
<211> LENGTH: 22
<212> TYPE: DNA
<213> ORGANISM: Artificial
<220> FEATURE:
<223> OTHER INFORMATION: one of the primer pairs for replacing
      residue 277 on the human factor IX cDNA.

<400> SEQUENCE: 20
ctaagggtgc gtccagttcc ag                                               22

<210> SEQ ID NO 21
<211> LENGTH: 20
<212> TYPE: DNA
<213> ORGANISM: Artificial
<220> FEATURE:
<223> OTHER INFORMATION: one of the primer pairs for replacing
      residue 338 on the human factor IX cDNA.
<220> FEATURE:
<221> NAME/KEY: misc_binding
<222> LOCATION: (1)..(20)

<400> SEQUENCE: 21
catgtcttgc atctacaaag                                                  20

<210> SEQ ID NO 22
<211> LENGTH: 20
<212> TYPE: DNA
<213> ORGANISM: Artificial
<220> FEATURE:
<223> OTHER INFORMATION: one of the primer pairs for replacing
      residue 338 on the human factor IX cDNA.
<220> FEATURE:
<221> NAME/KEY: misc_binding
<222> LOCATION: (1)..(20)

<400> SEQUENCE: 22
ctttgtagat gcaagacatg                                                  20

<210> SEQ ID NO 23
<211> LENGTH: 19
<212> TYPE: DNA
<213> ORGANISM: Artificial
<220> FEATURE:
<223> OTHER INFORMATION: factor IX specific forward primer
<220> FEATURE:
<221> NAME/KEY: misc_binding
<222> LOCATION: (1)..(19)

<400> SEQUENCE: 23
ggaagcagta tgttgatgg                                                   19

<210> SEQ ID NO 24
<211> LENGTH: 20
<212> TYPE: DNA
<213> ORGANISM: Artificial
<220> FEATURE:
<223> OTHER INFORMATION: factor IX specific reverse primer
```

```
<220> FEATURE:
<221> NAME/KEY: misc_binding
<222> LOCATION: (1)..(20)

<400> SEQUENCE: 24
tggttcacag gacttctggt                                                    20
```

RECOMBINANT HUMAN FACTOR IX AND USE THEREOF

CROSS-REFERENCE TO RELATED APPLICATIONS

This application is a Divisional of Ser. No. 11/935,779, now U.S. Pat. No. 7,700,734, filed on Nov. 6, 2007, which claims priority to provisional 60/884,129 filed on Jan. 9, 2007, all of which is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention relates to a recombinant human factor IX protein, and a nucleic acid sequence encoding thereof. The present invention also relates to a method for treating hemophilia.

BACKGROUND OF THE INVENTION

In the developed world, the current therapeutic choices for treatment of hemophilia patients comprise prophylactic and on-demand replacement therapy (Lofqvist T. et al., J. Intern. Med. 1997; 241:395-400) with either plasma-derived or recombinant coagulation factor concentrate (Lippert B. et al., Blood Coagul. Fibrinolysis. 2005; 16:477-485). Standard treatment for Hemophilia is infusions of protein concentrates to replace the defective clotting factor. The amount infused depends upon the severity of bleeding, the site of the bleeding, and the body size of the patient. People with severe forms of the disease may be treated by regular prophylactic infusions. The outcome is good with treatment and management, so most people with hemophilia are able to lead relatively normal lives. However, the high cost and limited availability of the recombinant protein make dosing of clotting factors a crucial issue in the treatment of hemophilia. In addition, the plasma-derived products run the risk for HIV and hepatitis B and C transmission, and the half-life of the infused protein in a patient is short, which results in the necessity for fairly frequent infusions (White G. C. et al., Transfus. Sci. 1998; 19:177-189).

Other treatments, such as gene therapy and tissue implant techniques are also under study as possible treatments (Hough C. et al., J. Thromb. Haemost., 2005; 3:1195-1205). One clinical trial of gene therapy in hemophilia patients showed only transient therapeutic increments of clotting factor expression due to generation of antibody against delivering vehicle (Manno C. S. et al., Nat. Med. 2006; 12:342-347). Therefore, gene therapy remains an investigational method with many obstacles to overcome before it can be widely used as treatment for hemophilia.

Hemophilia B is caused by a deficiency of a blood plasma protein called factor IX that affects the clotting property of blood. The disorder is caused by an inherited X-linked recessive trait, with the defective gene located on the X chromosome. Thus, the disorder occurs primarily in males. Hemophilia B occurs in about 1 out of 30,000 men.

Human factor IX is a vitamin K-dependent zymogen which plays an important role in blood coagulation. Factor IX circulates as a 415-amino acid single chain zymogen with a molecular mass of 55,000 daltons and is present in normal plasma at approximately 5 μg/ml.

Recombinant factor IX products offer greatly reduced risk for HIV and hepatitis B and C transmission. If recombinant factor IX with enhanced clotting activity can be generated through genetic engineering of factor IXDNA, it will not only lower the cost for the clotting factor but also reduce the dose of it in managing patients with hemophilia. Moreover, this method will also provide a more efficient tool for gene therapy trials in patients with hemophilia.

SUMMARY OF THE INVENTION

Figure 1:
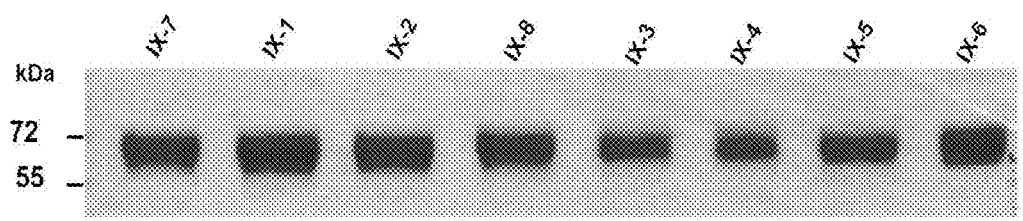
FIG. 1 shows the SDS-PAGE analysis of purified recombinant factor IX. Purified proteins (4 μg/lane) from Wild type (IX-7) and mutants IX-1, IX-2, IX-8, IX-3, IX-4, IX-5 and IX-6 were subjected to sodium dodecyl sulfate polyacrylamide gel electrophoresis (SDS-PAGE). Samples were run under non-reducing conditions. Factor IX protein bands were visualized by Commassie blue staining. The concentration of affinity-purified recombinant wild type and alanine-replaced factor IX was determined by the BCA™ protein assay kit (Pierce, Rockford, Ill., USA) using bovine γ-globulin (cat.#23212, Pierce) to generate a standard curve for calculating the protein concentrations.

The present invention provides a recombinant human factor IX protein having substitution of amino acid residue of SEQ ID NO: 7 at amino acid position selected from the group consisting of 86, 277 and 338, provided that the substitution at amino acid position 338 is excluded.

The present invention further provides an isolated nucleic acid encoding a recombinant human factor IX protein having nucleic acid sequence shown in SEQ ID NO: 9, 10, 11, 12, 13 or 14.

The present invention further provides a pharmaceutical composition comprising: (a) a human factor IX protein of the present invention, and (b) a pharmaceutically acceptable carrier, excipient, or diluent.

The present invention further provides a method for generating a human factor IX protein of the present invention in vivo comprising: (a) constructing a vector carrying a nucleic acid encoding the human factor IX protein; and (b) administering the vector to a mammalian.

The present invention further provides a method for treating hemophilia comprising administering to a patient in need of such treatment with an effective amount of the protein of the present invention.

DETAILED DESCRIPTION OF THE INVENTION

The present invention provides a recombinant factor IX with higher activity than wild type factor IX, and it allows less protein injection than the latter into hemophilia to reach the therapeutic level.

The present invention provides a new factor IXDNA sequence that would express a factor IX protein with a higher clotting activity than the DNA sequence expressing wild type factor IX when delivered into animals by various means such as viral vectors.

Using recombinant techniques, factor IX with simultaneously double or triple alanine replacement at positions 86, 277, and 338 exhibited 2~14 times better clotting activity than wild type recombinant factor IX (IX-7). In an attempt to understand the causes contributing to the increased clotting activity of these factor IX variants, several functional parameters were determined. Table 1 demonstrates that the increased clotting activity was factor VIIIa-dependent and was attributed to the enhanced affinity of factor IX for factor VIII and an increased $k_{cat}$ and decreased $K_M$ for factor X.

Accordingly, the present invention provides a recombinant human factor IX protein having substitution of amino acid residue of SEQ ID NO: 7 at amino acid position selected from the group consisting of 86, 277 and 338, provided that the single substitution at amino acid position 338 is excluded. The present proteins have alanine residue substitution at amino acid sequence of wild type factor IX, wherein the substitution is at the amino acid position selected from the group consisting of 86, 277, and 338.

The term "amino acid" used herein is a molecule that contains both amine and carboxyl functional groups. In biochemistry, this term refers to alpha-amino acids with the general formula $H_2NCHRCOOH$, where R is an organic substituent. In the alpha amino acids, the amino and carboxyl groups are attached to the same carbon, which is called the α-carbon. The various alpha amino acids differ in which side chain (R group) is attached to their alpha carbon. In general, the standard amino acids such as alanine, asparagine, aspartic acid, glutamine, glutamic acid, glycine, histidine, isoleucine, leucine, methionine, phenylalanine, serine, threonine, tryptophan, tyrosine or valine can be used as a substituted amino acid. In a preferred embodiment, the substituted amino acid residue is alanine.

In a more preferred embodiment, the protein of the present invention has SEQ ID NO: 1, 2, 3, 4, 5 or 6. In the most preferred embodiment, the protein of the present invention has SEQ ID NO: 6.

The substitution creates the non-naturally occurring human factor IX exhibiting from 2 to 14 folds more than wild type factor IX protein's clotting activity (Table 1). The protein has enhanced affinity for cofactor, factor VIIIa. In an embodiment, the recombinant human factor IX protein has $K_d$ values of 0.1~0.5 nM. In an embodiment, the recombinant human factor IX protein has $K_M$ values of 32~128 nM, preferably 32~56 nM (Table 2).

The present invention also provides an isolated nucleic acid encoding a recombinant human factor IX protein having nucleic acid sequence shown in SEQ ID NO: 9, 10, 11, 12, 13 or 14. In a preferred embodiment, the nucleic acid has SEQ ID NO: 11, 12 or 13. In a more preferred embodiment, the nucleic acid has SEQ ID NO: 14.

The present invention further provides a pharmaceutical composition comprising: (a) a human factor IX protein of the present invention; and (b) a pharmaceutically acceptable carrier, excipient, or diluent.

Besides in vitro expression and analysis of their biological properties, the present invention also relates to using mouse model to evaluate the potential role of the alanine variants. The hemophilia B mouse offers a model that allows the physiological role of these variant factor IXs to be studied. To estimate the degradation pathway of factor IX, these human factor IX proteins is injected into the tail vein of hemophilia mouse and the characteristics of these mutant proteins is observed.

Hydrodynamics-based delivery of naked plasmid DNA to liver can generate therapeutic plasma levels of transgene products in mice. This technology is used to deliver the DNA encoding the wild type and variant factor IX genes to hemophilia B mice.

Systemic delivery of therapeutic transgenes by viral vectors can potentially lead to long-term transgene expression (Miao C. H. et al., Mol. Ther. 2001; 3:947-957). But the efficiency of gene transfer to hepatocytes is poor. The recombinant AAV delivery system garnered enthusiastic support when it demonstrated efficacy in initial preclinical studies in the hemophilia B animal models (Davidoff A. M. et al., Mol. Ther. 2005; 11:875-888). Two clinical studies were initiated using an AAV serotype 2 vector to deliver factor IX to the muscle (Manno C. S. et al., Blood. 2003; 101:2963-2972) by direct intra muscular injection and to the liver via hepatic artery infusion (Manno C. S. et al., Nat. Med. 2006; 12:342-347), In the muscle trial, plasma level of factor IX generally did not raise above 1%, whereas levels of up to 12% were detected in the plasma of single patient treated by hepatic artery delivery of the AAV vector, However the increase was followed by a transient rise in serum transaminase levels and loss of factor IX expression, probably due to pre-existing host immunity to AAV capsid proteins that targeted the transduced cells. Because the recombinant IX-6 has higher activity than wild type (IX-7) in our mouse model, it could be possible to reduce the injection quantity of viral particles and reach the same factor IX activity.

Accordingly, the present invention also provides a method for generating a human factor IX protein of the present invention in vivo comprising:

(a) constructing a vector carrying a nucleic acid encoding the human factor IX protein; and (b) administering the vector to a mammalian.

In a preferred embodiment, the mammalian is human.

The term "administration" used herein is not limited but includes via vector, plasmid, liposome, DNA injection, electroporation, gene gun, intravenously injection or hepatic artery infusion.

The present invention further provides a method for treating hemophilia comprising administering to a patient in need of such treatment with an effective amount of a protein of the present invention.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

Example

The examples below are non-limiting and are merely representative of various aspects and features of the present invention.

Materials

Purified human factors VIIa, XIa, Xa, and X, and polyclonal goat anti-human factor IX antibodies (cat. #GAFIX-AP) were purchased from Enzyme Research Laboratory (ERL, South Bend, Ind., USA). Phosphatidylcholine (PC), phosphatidylserine (PS) and ITS (Insulin-Transferrin-Sodium selenite) media supplements used in serum free media were from Sigma Chemical Co. (St. Louis, Mo., USA). Preparation of tissue factor and PCPS phospholipids were described previously (Chang Y J, et al., Biochemistry, 1999: 10940-10948). Factor IX deficient plasma, Spectrozyme FXa, and Spectrozyme FIXa were purchased from American Diagnostica Inc. (Greenwich, Conn., USA). All the restriction endonucleases and polymerases were products of the New England Biolabs, Inc. (Beverly, Mass., USA). Geneticin (G418) was from CalBiochem (Merck KGaA, Darmstadt, Germany). A Vmax microtiter plate reader equipped with a thermal controller (Molecular Devices Corp., Menlo Park, Calif., USA) was used for all spectrophotometric assays. QAE-Sephadex A50, and Resource Q were from Amersham (Amersham Pharmacia BioTech, UK, Bucks, England).

Methods

In-Vitro Mutagenesis, Expression and Purification of Factor IX

Site-specific mutagenesis was performed on the human factor IX cDNA by a PCR-based method (QuickChange, Stratagene, Boston, USA) using primer pairs for replacing the codons at residues 86, 277 or 338 with those for alanine. The sequences of the primers are IX86 (SEQ ID NO: 17) pairing with IX86T7 (SEQ ID NO: 18) for replacing residue 86; IX277 (SEQ ID NO: 19) pairing with IX277-2 (SEQ ID NO: 20) for replacing residue 277, and IX338 (SEQ ID NO: 21) pairing with IX338D (SEQ ID NO: 22) for residue 338. With these primer pairs, 7 different factor IX cDNA's were generated, fully sequenced, and together with wild type factor IX (IX-7) subcloned into PCR3™-Uni (Invitrogen, CA, USA) for expression in human 293 cells under the control of cytomegalovirus. Of the 7 recombinant factor IX mutants, three are single replacement mutants with alanine substitution at residues 86, 277 or 338 (SEQ ID NO: 1, SEQ ID NO: 2 or SEQ ID NO: 8, respectively), another three are double replacement mutants with alanine substitutions at 86 plus 277 (SEQ ID NO: 3), 86 plus 338 (SEQ ID NO: 4) and 277 plus 338 (SEQ ID NO: 5), and the other is triple replacement mutant with 86, 277 and 338 all replaced by alanine (SEQ ID NO: 6). Identification of cell clones expressing the recombinant proteins was by ELISA (see below) using the commercially available factor IX specific antibodies. Expansion of the correct cell clones in serum free media to large quantity and purification of the recombinant proteins were performed as described previously. Briefly, one liter of the cultured supernatant was adjusted to 5 mM benzamidine and 4 mM EDTA and subjected to centrifugation at 4,350 rpm (HA6000, Sorvall RC-3C Plus, DuPont) for 30 mM at 4° C. After removal of cell debris, the supernatant was passed through a QAE-Sephadex A50 column (30 ml, 5×2.5 cm) equilibrated with TBS/EDTA (20 mM Tris-Cl, pH 7.5, and 150 mM NaCl/4 mM EDTA). After washing the column with 1 liter of TBS containing 5 mM benzamidine, factor IX was eluted with a gradient of 0~30 mM $CaCl_2$ in TBS/1 mM benzamidine. Fractions containing factor IX were identified by ELISA (see below), pooled, dialyzed against 100-fold excess volumes of 50 mM Tris-Cl, pH 7.5, and filtered through a 0.22-μm syringe filter (Millipore, Cork, Ireland). Approximately 100 ml of the QAE-eluent was loaded on to a Resource Q column (1 ml, Akta FPLC purifier, Amersham Biosciences). After washing in buffer containing 50 mM Tris-Cl, pH 7.5, the column was eluted with a gradient of NaCl (0~1 M) in 50 mM Tris-Cl, pH 7.5. Factor IX was eluted at fractions of approximate 250 mM NaCl. The purified recombinant factor IX proteins were verified by SDS-PAGE followed by staining with Coomassie blue.

Enzyme-Linked Immunosorbent Assay (ELISA) and Clotting Activity Assay

The protein mass of wild type and the alanine-replaced human factor IX (hFIX) in cultured supernatant and in mouse plasma was determined by ELISA using polyclonal antibodies to human factor IX. The antibodies are species-specific polyclonal anti-hFIX antibodies that do not cross-react with murine factor IX. Pooled plasmas of at least 20 healthy individuals were used in serial dilutions in parallel experiments to prepare standard curves for calculation of the level of factor IX. The standard curves from the pooled plasma paralleled to those derived from the purified plasma factor IX (IMMUNINE, Baxter AG, Vienna, Austria).

The function of the recombinant factor IX proteins was determined by their clotting activities in the one-stage activated partial thromboplastin time (aPTT) assays. Pooled normal plasma in serial dilutions was used as assay standards. The standard curves of the clotting assays parallel to those derived from the purified plasma factor IX (IMMUNINE) and the recombinant factor IX (BeneFIX, Genetics Institute, Inc. Cambridge Mass., USA). The specific activity of a sample was defined as the clotting activity divided by its mass. The factor IX protein mass and clotting activity in pooled normal human plasma was assumed to be 5 μg/ml.

Activation of Factor Ix by Factor XIa and by Factor VIIa and Tissue Factor (VIIa·Tf) Complex The activation of factor IX by factor XIa in the presence of TBS/5 mM $CaCl_2$ was performed at an enzyme to substrate ratio of 1:200. Aliquots from the reaction mixtures were withdrawn at timed-intervals, placed in a solution containing 1% SDS and 2 mM EDTA to stop the reaction, adjusted in gel loading buffer (final concentrations: 50 mM Tris-Cl, pH 6.8, 2 mM EDTA, 1% SDS, 8% glycerol, and 0.025% Bromophenol blue), and subsequently subjected to SDS-PAGE analysis. The activation of factor IX by the VIIa·TF complex was performed at an enzyme to substrate ratio of 1:80 and in TBS/5 mM of $CaCl_2$. Aliquots from the reaction mixtures were withdrawn at timed-intervals and resolved by SDS-PAGE analysis.

Interaction of Factor IXa with Factor X

Factor IXa was prepared by activation with factor XIa as described above. The concentration of the factor IXa molecules was determined by titration with antithrombin III (ATIII) as described previously (Chang Y J, et al., Journal of Biological Chemistry. 2002; 277:25393). Interaction of factor IXa with factor X was analyzed by monitoring kinetically the hydrolysis of Spectrozyme FXa by activated factor X generated by factor IXa in the absence and presence of factor VIIIa. Briefly, when without factor VIIIa, factor IXa (10 nM) was incubated with PCPS at room temperature for 5 mM before different concentrations of factor X (0-1 µM) and 0.5 mM Spectrozyme FXa were added and the reaction was recorded as the absorbance change of the mixture according to the incubation time. The final volume was 100 µl and the reaction was performed at 37° C. in buffers containing 0.01% BSA and 40 µM PCPS in TBS/5 mM $CaCl_2$(TBS/$CaCl_2$/BSA/PCPS). The interaction of factor IXa with factor X in the presence of factor VIIIa was performed by incubation of 25 µl of factor VIIIa (freshly prepared) with an equal volume of FIXa diluted and preincubated in TBS/$CaCl_2$/BSA/PCPS, and a 50 µl of a reaction mixture containing PCPS, Spectrozyme FXa and factor X added subsequently. The factor Xa activity generated by the factor IXa-factor VIIIa complex (the intrinsic tenase activity) in the mixture was detected kinetically on the microtiter plate reader. Final concentrations were 0.25 nM for wild type or mutant factor IXa, 0.4 nM for factor VIIIa, 40 µM for PCPS, 0-200 nM for factor X, and 0.5 mM for Spectrozyme FXa. The factor IXa activity was calculated by the following equation as described previously. Absorbance $(A_{405})=at^2+bt+c$ Interaction of Factor IXa with Factor VIIIa Binding experiments were performed by monitoring the intrinsic tenase activity at limiting concentrations of factor VIIIa. Twenty-five microliters of freshly prepared factor VIIIa (0.4 nM) were incubated with 25 µl of different concentrations of wild type or mutant factor IXa (0-20 nM) to form the intrinsic tenase complex. Activity of the intrinsic tenase complex formed by binding of factor VIIIa to factor IXa was then measured by the addition of 50 µl of a mixture of factor X and Spectrozyme FXa in a reaction buffer containing TBS/Ca/PCPS/BSA. Final concentrations were factor VIIIa, 0.1 nM, PCPS, 40 µM, factor X, 100 nM, Spectrozyme FXa, 0.5 mM, and factor IXa, 0~15 nM. Experiments were performed in duplicate for 3 independent reactions, and curves were fitted using all data points. The $K_d$ values were derived by calculations according to the following equation as described previously (Chang Y J, et al., Journal of Biological Chemistry. 2002; 277:25393).

$$[IXa-VIIIa] = \frac{[IXa]_t + [VIIIa]_t + K_d}{2} - \frac{\sqrt{([IXa]_t + [VIIIa]_t + K_d)^2 - 4[IXa]_t[VIIIa]_t}}{2}$$

Interaction of Factor Ix with Antithrombin III (ATIII)

The inhibition of factor IXa by ATIII was performed by gel analysis of the enzyme-inhibitor complex. 0.53 µM factor IXa and 0.53 µM ATIII were incubated at 37° C. in 100 µl of TBS/5 mM $CaCl_2$ with or without 0.01 unit/ml heparin. Aliquots (20 µl) of the reaction mixtures were withdrawn at different time intervals (0, 5, 10, 20, and 30 mM), mixed with gel loading buffer (final concentration: 50 mM Tris-Cl, pH 6.8, 2 mM EDTA, 1% SDS, 8% glycerol, and 0.025% Bromophenol blue) and developed by SDS-PAGE followed by staining with silver.

Animal Experiments

All the animal experiments described below followed standard procedures Animals were treated according to the guidelines of the National Taiwan University in Taiwan or the National Institutes of health guidelines for animal care and the guidelines of the Children's Hospital and Regional Medical Center at Seattle, USA. Hemophilia B mice of C57BL/6 strain background were originally obtained from Dr. Darrel Stafford (Biology Department, University of North Carolina at Chapel Hill, N.C., USA) and Dr. Katherine High (The Children's Hospital of Philadelphia, Pa., USA).

Protein Infusion into Hemophilia B Mice

Mice were anesthetized with 2.5% Avertin and injected intravenously with 0.25 µg/g body weight of recombinant proteins IX-6 (SEQ ID NO: 6), IX-7 (SEQ ID NO: 7) and IX-8 (SEQ ID NO: 8) to reach a hypothetical circulating level of 5 µg/ml, assuming the total plasma volume of a mouse be estimated by 1/10 of body weight. At 5 min, 15 min and 2 h after injections, mice were sacrificed and blood was collected into 3.8% sodium citrate (9:1 v/v) from the inferior vena cava. Plasma were prepared by centrifugation at 8,000 rpm (Eppendorf, 5415R) at room temperature for 10 minutes and subjected to analyses for protein mass by ELISA and clotting activity by aPTT assay.

Hydrodynamic Injection and Measurement of Human Factor IX Expression in Hemophilia B Mice The cDNA's coding for recombinant factor IX (SEQ ID NOs: 9-16) were individually subcloned into pBS-HCRHP1-A (Miao C. H. et al., Mol. Ther. 2001; 3:947-957), for optimal expression in the liver of hemophilia B mice under the control of the human apolipoprotein E/C-I gene locus control region and the human alpha-1 antitrypsin promoter, as well as the truncated human factor IX intron 1 and the bovine growth hormone polyadenylation signal sequence for improved protein expression. Mice were anesthetized with 2.5% Avertin and aliquots (50-100 µg) of these expression plasmids (pBS-HCRHP1-A-FIX) were dissolved in 2 ml PBS (phosphate-buffered saline) and injected into the tail vein of 17~24 g mice over a period of 6~8 seconds. Each experiment with respective plasmid was repeated several times with at least two different batches of plasmid DNA prepared at different times. Blood samples were taken from inferior vena cava when necessary and made into plasma by dilution with 1/10 (v/v) of 3.8% sodium citrate. Human factor IX protein levels and clotting activity expressed and present in the mouse plasma were measured by ELISA and aPTT, respectively. Liver tissues were also prepared and measured for factor IX expression by ELISA. Total liver (1~1.7 g) were homogenized in the presence of 2 ml of T-PER tissue protein extraction reagent (cat. #78510, Pierce) containing 5 µl/ml of protease inhibitor cocktail (Sigma). After centrifugation, the total protein in the supernatant of the extract was about 31.8±3.5 mg/ml which was subjected to ELISA for human factor IX levels.

Gene Transfer Experiments Using Pseudotyped ssAAV2/8 Vector

The coding sequences of IX-6 (SEQ ID NO: 14), and IX-7 (SEQ ID NO: 15) cDNA (1.4-kb in length, without 3' untranslated region) were individually subcloned into pBS-HCRHP1-A, subsequently excised as a 4.3-kb SpeI fragment containing the entire expression cassette (enhancer, promoter, factor IX coding region and intron 1, and bovine growth hormone polyadenylation signal) and subcloned into pAAV-MCS (Stratagene, La Jolla, Calif.) at the NotI site converted to XbaI by ligation with linkers. The resultant plasmids consist of the entire expression cassette (4.3-kb SpeI fragment) flanked by the inverted terminal repeats (ITRs) of AAV2. The ssAAV2/8 vector carrying individual IX-6 and IX-7 expression cassettes were used to produce AAV viral particles by the Triple transfection method as previously described (Xiao X, et al. J. Virol. 1998; 72:2224-2232). The vector titers were determined by quantitative polymerase chain reaction (LightCycler 480, Roche Applied Science, Mannheim, Germany) using factor IX specific primers (forward: SEQ ID NO: 23 and reversed: SEQ ID NO: 24) and expressed as vector genome (vg)/ml. Tail vein administration of viral particles into hemophilia B mice was performed with vector doses of $4 \times 10^{12}$, $4 \times 10^{11}$ or $8 \times 10^{10}$ vg/kg body weight. These mice were sacrificed 2 weeks after tail vein injection of AAV particles. Blood samples were collected from inferior vena cava for plasma preparation. Human factor IX protein levels and clotting activities expressed and present in the mouse plasma were measured by ELISA and aPTT, respectively.

Results

Engineered Recombinant Factor IX Proteins Exhibited Higher Clotting Activity than Wild Type Factor Ix (IX-7)

To search for factor IX variants with augmented clotting function, we selected 3 amino acid positions 86, 277, and 338, of human factor IX and replaced them singly or in combination with alanine. We expressed a total of 7 alanine-replaced factor IX variants in human 293 kidney cells. The expression levels of the mutated factor IX were quite equivalent to that of the wild type factor IX (IX-7) and approximated 0.08~0.5 µg/24 h/$10^6$ cells. After purification, all the recombinant factor IX proteins revealed as a single band in SDS-PAGE with a mobility similar to that of plasma derived factor IX (FIG. 1). The identity of the recombinant proteins were verified and confirmed by amino acid sequence analysis revealing the first 5 residues of each recombinant (data not shown). The integrity of the IX-7 and alanine mutants was further investigated by activation of the recombinant factor IX proteins with factor XIa and with the factor VIIa and tissue factor (VIIa·TF) complex, and inhibition by antithrombin III in the presence and absence of heparin. These experiments revealed no apparent differences between IX-7 and all the 7 alanine recombinants (data not shown). We conclude that alanine substitutions at positions 86, 277 and 338 did not alter the global structure of factor IX.

The clotting activity of the purified factor IX recombinants was shown in Table 1. Recombinant IX-7 was fully active and had a specific activity of 94%. All the factor IX mutants were also functional and had 1.1~13 times more clotting activity than IX-7. Among all, factor IX-6 was the most active and had 13 times better than IX-7's clotting activities.

TABLE 1

Specific Clotting activity of purified factor IX.[a]

|      | Clotting act. (µg/ml) | Sp. Act. (%) |
|------|-----------------------|--------------|
| IX-7 | 4.72 ± 0.81           | 94 ± 16      |
| IX-1 | 5.38 ± 0.50           | 115 ± 10     |
| IX-2 | 5.96 ± 0.77           | 130 ± 15     |
| IX-8 | 18.08 ± 0.14          | 362 ± 3      |
| IX-3 | 6.34 ± 0.34           | 122 ± 7      |
| IX-4 | 8.51 ± 2.06           | 199 ± 41     |
| IX-5 | 9.38 ± 3.30           | 188 ± 66     |
| IX-6 | 66.04 ± 2.84          | 1293 ± 57    |

[a]The recombinant factor IX was purified from 0.5~1 liters cultured supernatant of stably-transfected HEK 293 cells. The purified factor IX concentration was determined by Biuret method (BCA protein assay kit, Pierce) as described in legend to FIG. 1 and diluted to 5 µg/ml. The clotting activity was determined by the aPTT assays. Pooled normal human plasma in serial dilutions was used to generate the standard curves. The factor IX concentration in the pooled plasma was estimated to be 5 µg/ml. The specific activity of a sample was defined as the clotting activity divided by its mass in concentration and presented as percentage. The experiments were repeated 2 times.

The Increased Clotting Activity of IX-6 Correlated with its Affinity for Factor VIIIa.

Enzymatic kinetics parameters were measured with the factor IXa recombinants to investigate the influence of the alanine substitution on the clotting function of factor IXa. We assume that factor tenase activity is proportional to the concentration of the factor IXa in complex with factor VIIIa (FIXa·FVIIIa). Therefore, one could monitor the generation of factor Xa by the FIXa·FVIIIa complex as an indication for the binding affinity of factor IXa for factor VIIIa and calculate the apparent dissociation constant ($K_d$). As shown in Table 2, the $K_d$'s for the three variants with single alanine mutations (IX-1, IX-2 and IX-8) and one of the variants with double mutations (IX-3) (1.20 nM-1.95 nM) are approaching that for IX-7 (2.44 nM). Surprisingly, the $K_d$'s for the two with double mutations (IX-4 and IX-5) and the one with triple mutations (IX-6) (0.4 nM, 0.34 nM and 0.19 nM, respectively) were significantly lower than those for the IX-7 or the three single mutations. There is a 10-fold dramatic difference in $K_d$ between IX-6 and IX-7. Moreover, it appears that IX-6 and factor VIIIa can form an efficient enzyme complex (0.144 nM) as compared with IX-7 and factor VIIIa (0.033 nM). These consequences, together with the better affinity between IX-6 and factor VIIIa than IX-7 and factor VIIIa, seem to justify the increased clotting activity of IX-6.

In the absence of factor VIIIa, the kinetic parameters, i.e., $K_M$ and $k_{cat}$ for all the recombinant mutants and IX-7 were very similar (Table 2), with $k_{cat}/K_m$ around 240.59~726.81 $M^{-1}$ $sec^{-1}$. The result indicates that without factor VIIIa, factor IXa is a rather inefficient enzyme in cleaving factor X, which has been observed for activated IX-7 and so does for these factor IXa mutants.

TABLE 2

Kinetic parameters of factor Xa generation in the absence and presence of factor VIIIa.

| | $K_M$ nM | $V_{max}$ nM FXa/min | Enzyme[a] nM | $K_{cat}$[b] | $k_{cat}/K_M$ ($M^{-1}sec^{-1}$) | $K_d$ nM |
|---|---|---|---|---|---|---|
| Without FVIIIa | | | | ×10$^{-4}$ | | |
| IX-7 | 756.8 ± 102.6 | 0.16 ± 0.04 | 10 | 2.62 ± 0.59 | 352.95 ± 109.17 | ND[#] |
| IX-1 | 531.9 ± 130.2 | 0.14 ± 0.03 | 10 | 2.25 ± 0.50 | 426.54 ± 35.84 | ND |
| IX-2 | 395.3 ± 43.0 | 0.07 ± 0.05 | 10 | 1.22 ± 0.86 | 303.64 ± 204.5 | ND |
| IX-8 | 479.8 ± 44.0 | 0.08 ± 0.04 | 10 | 1.37 ± 0.61 | 280.05 ± 108.00 | ND |
| IX-3 | 290.1 ± 54.58 | 0.12 ± 0.05 | 10 | 1.95 ± 0.77 | 726.81 ± 298.62 | ND |
| IX-4 | 479.0 ± 87.5 | 0.08 ± 0.02 | 10 | 1.35 ± 0.41 | 278.40 ± 36.18 | ND |
| IX-5 | 681.4 ± 151.1 | 0.10 ± 0.07 | 10 | 1.64 ± 1.11 | 240.59 ± 161.64 | ND |
| IX-6 | 742.8 ± 18.0 | 0.17 ± 0.05 | 10 | 2.82 ± 0.85 | 380.68 ± 121.26 | ND |
| With 0.4 nM FVIIIa[c] | | | | ×1 | ×10$^8$ | |
| IX-7 | 54.04 ± 5.25 | 27.81 ± 0.66 | 0.033 | 14.17 ± 0.34 | 2.64 ± 0.21 | 2.44 ± 1.06 |
| IX-1 | 55.39 ± 10.57 | 15.11 ± 0.90 | 0.049 | 5.09 ± 0.30 | 0.93 ± 0.12 | 1.42 ± 0.48 |
| IX-2 | 44.27 ± 2.15 | 29.74 ± 0.42 | 0.056 | 8.89 ± 0.13 | 2.01 ± 0.07 | 1.20 ± 0.08 |
| IX-8 | 44.79 ± 8.33 | 28.41 ± 3.34 | 0.052 | 9.08 ± 1.07 | 2.04 ± 0.14 | 1.32 ± 0.24 |
| IX-3 | 35.17 ± 3.18 | 34.12 ± 1.13 | 0.039 | 14.56 ± 0.48 | 4.16 ± 0.28 | 1.95 ± 0.44 |
| IX-4 | 80.95 ± 13.15 | 46.78 ± 8.02 | 0.106 | 7.36 ± 1.26 | 0.91 ± 0.04 | 0.40 ± 0.11 |
| IX-5 | 116.53 ± 12.45 | 145.81 ± 14.03 | 0.114 | 17.93 ± 6.72 | 2.12 ± 0.44 | 0.34 ± 0.15 |
| IX-6 | 46.01 ± 10.53 | 52.26 ± 10.22 | 0.144 | 5.07 ± 1.19 | 1.33 ± 0.10 | 0.19 ± 0.07 |

[a] The concentration of factor IXa-VIIIa complex was derived from experimental conditions and observed $K_c$
[b] $k_{cat} = V_{max}$ [enzyme] the units are M FXa, $M^{-1}$FIXa (or FIXa-FVIIIa), $s^{-1}$
[c] The reaction was incubated with 0.4 nM factor VIIIa and 0.25 nM factor IXa to activate 0-200 nM factor X in the presence of 0.5 mM Spactrozyme FXa, 40 µM PCPS and 5 mM Ca2+.
[#] ND: Not determined To evaluate the effectiveness of the recombinant factor IX in vivo, we infused IX-6, IX-7, and IX-8 proteins into hemophilia B mice and followed the protein levels and clotting function of the proteins by analyzing the plasma samples at timed intervals. As shown in Table 3, when approximately 1 µg/ml of IX-7 protein was detected in the plasma of the hemophilia B mice at 5 min after tail vein injection of 10 µg recombinant protein in 20 g mice, the level decreased to 76% initial levels at 15 min and to 18% initial at 2 h. The circulating factor IX-7's clotting activity at each timepoint ranged around 121~483% protein mass. Parallel experiments with IX-6 and IX-8 revealed that while comparable to IX-7's protein levels were detected at each time point in mice infused with IX-8 and IX-6, the mice infused with recombinant IX-8 exhibited 2.4 (5 min's sample) ~3.67 (2 h's) times, respectively, more clotting function than those infused with IX-7. In consistent with in-vitro's experimental findings with IX-6, hemophilia B mice infused with IX-6 exhibited a much higher than IX-7's activity, approximately 2.6~7.5 times more than IX-7's specific activity throughout each time point [IX-7 versus IX-6, (2.91/1.15) versus (12.05/0.72) for 5 min's data as an example].

TABLE 3

Time course study of plasma factor IX levels in mice infused with recombinant factor IX proteins.*

| | IX-7 (n = 4) | | IX-8 (n = 2) | | IX-6 | | |
|---|---|---|---|---|---|---|---|
| | Clotting act. | IX:Ag | Clotting act. | IX:Ag | Clotting act. | IX:Ag | |
| | µg/ml (% of first time point) | | | | | | |
| 5 min. | 2.91 ± 1.2 | 1.15 ± 0.2 (100) | 6.98 ± 1.4 | 0.92 ± 0.1 (100) | 12.05 ± 4.4 | 0.72 ± 0.1 (100) | (n = 5) |
| 15 min. | 2.63 ± 1.0 | 0.88 ± 0.3 (76) | 5.24 ± 2.7 | 0.86 ± 0.1 (94) | 6.74 ± 1.4 | 0.55 ± 0.2 (77) | (n = 4) |
| 120 min | 0.64 ± 0.4 | 0.21 ± 0.2 (18) | 2.35 ± 0.2 | 0.36 ± 0.0 (39) | 4.80 ± 3.1 | 0.45 ± 0.1 (62) | (n = 3) |

*Approximately 10 µg factor IX was injected into each mouse to reach hypothetical protein concentration of 5 µg/ml plasma. Blood samples were taken at different time points after injection and subjected to ELISA and clotting assay. Standard curves were derived from serial dilutions of normal plasma in parallel experiment. ELISA system used pAb from ERL (Gafix-AP160) as coating antibody and ERL pAb-HRP (Gafix-HRP) as detecting antibody. Normal plasma factor IX concentration is assumed to be 5 µg/ml.

Gene Delivery to Hemophilia B Mice by Hydrodynamic Injection Method

Figure 2:
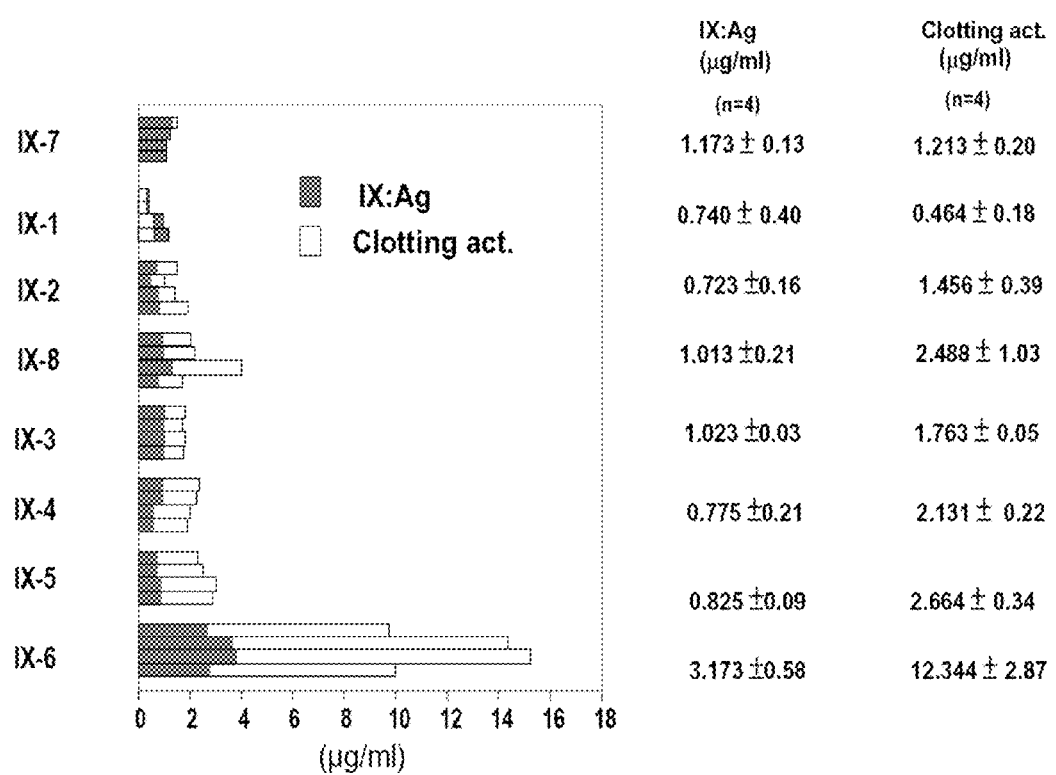
FIG. 2 shows human factor IX levels in hemophilia B mice at 24 hours after hydrodynamic treatment with pBS-HCRHP1-A-FIX (see "Method"). Male hemophilia B mice (20 μg body weight) were subjected to hydrodynamic shock by tail vein injection of 2 ml of 50 μg DNA in 6-8 seconds. The mice were recovered and sacrificed 24 h after injection for collection of blood plasma for clotting activity and protein level determination (IX:Ag) by Enzyme-linked ImmunoSorbent assay (ELISA). Each bar represents the data of individual mouse. Standard curves for ELISA and for clotting activity were derived in parallel experiments from serial dilutions of normal plasma pooled from 20 healthy donors. The factor IX protein level and clotting activity in the pooled plasma were assumed to be 5 μg/ml.

The efficacy of the factor IX mutants for the treatment of hemophilia B was also evaluated by the method of hydrodynamic injection of expression plasmids carrying individual cDNAs into hemophilia B mice for expression of the factor IX mutants predominantly by the liver. The expression levels were measured 24 h after DNA injection and shown in FIG. 2 and Table 4. Recombinant IX-7 and all the alanine replacement mutants except IX-6 were expressed and secreted into plasma at a protein level of 0.7~1.17 µg/ml and clotting activity of 0.46~2.26 µg/ml. IX-6 had reproducibly higher protein levels (3.22±0.58 µg/ml, n=4) and clotting activities (12.34±2.87 µg/ml, n=4) than IX-7 and the other alanine mutants. Interestingly, IX-6 also had 6 times (clotting activity) and 2 times (specific activity, i.e., IX:Ag/clotting) higher activity than IX-8. The higher factor IX protein levels found in mice injected with IX-6 DNA than with IX-7 and the other mutants was not observed with the cell culturing expression system which indicated that IX-7 and IX-6 were synthesized to similar levels. To further investigate possible explanations for the higher plasma factor IX protein levels in the mice injected with IX-6 than with IX-7 DNA, we extracted and quantified the intracellular and circulating factor IX in the liver and plasma, respectively. As shown in Table 4 approximately equal amount of factor IX was extracted from the liver of mice treated with IX-6 and IX-7 DNA (1.18 and 1.36 µg/g liver, respectively, p=0.43). These data indicated that IX-6 DNA- and IX-7 DNA-injected mice had comparable amount of intracellular factor IX in the liver. Interestingly, the IX-6 DNA-treated mice had statistically more circulating factor IX than IX-7 DNA-treated mice (1.5 times difference, p<0.01, n=7~10). More importantly, the plasma clotting activity of IX-6 DNA-mice is 15 times higher than that of the IX-7 DNA-treated mice (4.88±2.12 µg/ml vs 0.31±0.15 µg/ml, Table 4).

TABLE 4

Factor IX levels in mice hydrodynamically injected with plasmids.*

| | Liver | | plasma | |
|---|---|---|---|---|
| | Total protein (mg) | IX: Ag (µg) | IX: Ag (µg/ml) | Clotting act. (µg/ml) |
| | | | | (Sp. Act. %) |
| IX-7 (n = 7) | 60.92 ± 7.02 | 1.34 ± 0.76 | 0.20 ± 0.08 | 0.31 ± 0.15 (154 ± 33) |
| IX-6 (n = 10) | 65.73 ± 7.76 | 1.60 ± 0.61 | 0.34 ± 0.10 | 4.88 ± 2.12 (1411 ± 357) |

*Hydrodynamic delivery of factor IX expression plasmids into hemophilia B mice. Male hemophilia B mice of 20 µg were subjected to hydrodynamic shock by tail vein injection of 2 ml of 100 µg DNA in 6-8 s. The mice were recovered and sacrificed 24 h after injection for collection of blood plasma for clotting assay by aPTT and protein levels by ELISA (IX: Ag). For ELISA system, plates were coated with pAb from ERL (Gafix-AP160) and ERL pAb-HRP (Gafix-HRP) was used as detecting antibody. Standard curve was derived from serial dilutions of normal plasma. Normal plasma factor IX concentration is assumed to be 5 ug/ml.

Gene Transfer Experiments Using Pseudotyped ssAAV2/8 Vector

Figure 3:
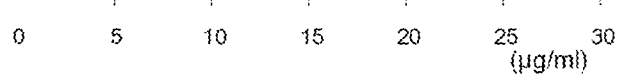
FIG. 3 shows results of factor IX expression by adeno-associated virus (AAV)-mediated gene transfer to hemophilia B mice. Construction of the rAAV2/8 vector carrying, individually, IX-6 and IX-7 was described in "Methods". Homozygous female hemophilia B mice (n=6, aged 8~14 weeks, weighing 16~18 g) were respectively injected intravenously with $4\times10^{12}$ vg/kg (a) $4\times10^{11}$ and $8\times10^{10}$ vg/kg (b) of the rAAV2/8 vehicles carrying IX-6 and IX-7 as indicated. Blood was collected 2 weeks after injection for measurement of factor IX protein level and clotting activity. Each group of mice was numbered according to age. Specific clotting activity presented as percentage was defined as the clotting activity measured for each sample divided by its mass (IX:Ag) measured by ELISA. Standard curves for ELISA and for clotting activity were derived in parallel experiments from serial dilutions of normal plasma pooled from 20 healthy donors. Factor IX protein level and clotting activity in the normal pooled plasma was assumed to be 5 μg/ml.
Figure 3:
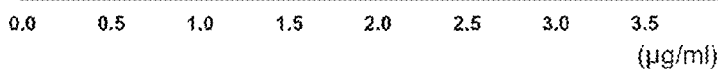

The efficacy of IX-6 in gene therapy was further investigated using viral vectors. The hemophilia B mice were injected intravenously with recombinant adeno-associated viral vectors (rAAV2/8) carrying individual IX-6, and IX-7 at a dose of $4 \times 10^{12}$ vg/kg. At two weeks after injection, the plasma factor IX protein level expressed by rAAV2/8 carrying IX-7 was about 2.3~7.8 µg/ml (n=5) (FIG. 3a). Compared with IX-7, the factor IX level expressed by rAAV2/8 carrying IX-6 reached 1.58~4.23 µg/ml (n=6). It appears that rAAV2/8 carrying IX-6 had lower factor IX protein level in mouse plasma than those carrying IX-7. In contrast, the specific clotting activity of IX-6 (495±109%) is 5 times higher than that of IX-7 (94±34%). We also evaluate the efficacy of IX-6 when delivered at lower doses of viral vectors (at $4 \times 10^{11}$ vg/kg and $8 \times 10^{10}$ vg/kg, respectively). As shown in FIG. 3b, the specific activity measured from mice injected with rAAV2/8 carrying IX-6 reach 1236±418% ($4 \times 10^{11}$ vg/kg) and 1129±479% ($8 \times 10^{10}$ vg/kg), and the specific activity measured in those mice injected with rAAV2/8 carrying IX-7 is approximately 192±24% ($4 \times 10^{11}$ vg/kg) and 246±116% ($8 \times 10^{10}$ vg/kg) for the two doses. At the lowest dose, one of the mice injected with IX-6 had 38% normal clotting activity and all 4 mice are above or nearly above the 10% therapeutic level. In contrast, the mice injected with IX-7 had only 5.6% and 7.4% normal clotting activity. The result further demonstrated that IX-6 can be an effective reagent when low dose of viral vector is preferred to reduce the formation of anti-viral antibodies.

The foregoing is illustrative of the present invention, and is not to be construed as limiting thereof. The invention is defined by the following claims, with equivalents of the claims to be included therein.

What is claimed is:

1. An isolated nucleic acid comprising the nucleic acid sequence of SEQ ID NO: 14, wherein said nucleic acid encodes a recombinant human Factor IX protein (FIX), that comprises the amino acid sequence of SEQ ID NO: 7, except for amino acid substitution(s) at one or more positions of SEQ ID NO:7 selected from the group consisting of: substitution at position 86, substitution at position 277, substitution at positions 86 and 277, substitution at positions 86 and 338, substitution at positions 277 and 338, and substitution at positions 86, 277 and 338.

2. A method for generating a human Factor IX (FIX) protein in vivo comprising: (a) constructing a vector carrying a nucleic acid encoding the human FIX protein; and (b) administering the vector to a mammal, wherein the human FIX protein comprises the amino acid sequence of SEQ ID NO: 7, except for amino acid substitution(s) at one or more positions of SEQ ID NO: 7 selected from the group consisting of: substitution at position 86, substitution at position 277, substitution at positions 86 and 277, substitution at positions 86 and 338, substitution at positions 277 and 338, and substitution at positions 86, 277 and 338.

3. The method of claim 2, wherein the mammal is human.

4. The method of claim 2, wherein the nucleic acid has a sequence shown in SEQ ID NO. 14.

5. The method of claim 2, wherein the administration is via vector, plasmid, liposome, DNA injection, electroporation or gene gun.

6. The method of claim 2, wherein the administration is via intravenous injection or hepatic artery infusion.

* * * * *